United States Patent
Glatman-Freedman et al.

(10) Patent No.: US 6,545,130 B2
(45) Date of Patent: *Apr. 8, 2003

(54) **MONOCLONAL ANTIBODIES TO *MYCOBACTERIUM TUBERCULOSIS* AND A MODIFIED ELISA ASSAY**

(75) Inventors: Aharona Glatman-Freedman, Irvington, NY (US); Arturo Casadevall, Pelham, NY (US)

(73) Assignee: Albert Einstein College of Medicine of Yeshiva University, Bronx, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/868,546

(22) Filed: Jun. 4, 1997

(65) Prior Publication Data

US 2002/0034763 A1 Mar. 21, 2002

(51) Int. Cl.$^7$ .......................... C07K 16/00; C12P 21/08
(52) U.S. Cl. .............................. 530/388.2; 530/388.1; 530/388.4; 530/391.1; 530/391.3; 530/391.7
(58) Field of Search .................. 530/388.1, 387.1, 530/388.2, 388.4, 388.26, 391.1, 391.3, 391.7

(56) References Cited

U.S. PATENT DOCUMENTS 5,770,719 A * 6/1998 Kapoor et al.

OTHER PUBLICATIONS

Glatman–Freedman et al p287 95$^{th}$ ASM General Mtg. Abstract E–36, 1995.*
Rambukkana et al, Scand. J. Immunol. 33:763–775, 1991.*
Glatman–Freedman et al, Infection & Immunity 68/1:335–341, 2000.*
Teitelbaum et al, PNAS, 95:15688–15693, Dec. 1998.*
Wagner et al, Med. Microbiol. Immunol 181/1:25–33 (Abstract Only), 1992.*
Ortalo–Magné, Microbiology 141:1609–1620, 1995.*
Catty et al In : Antibodies, vol. II, IrL Press at Oxford University pp. 97–154, 1989.*
Tijssenin "Practice and theory of enzyme immunoassays", Elsevier Science Publishers B. V. 1985 , pp. 117–121.*
Glatman–Freedman et al 1998 Clin. Microbiol. Rev. 11(3):514–532, 1998.*
Cho et al J. Clin. Microbiol, 30(12):3065–3069, 1992.*
Rambukkana et al. Scand. J. Immunol 33:763–775, 1991.*
Schöningh et al J. Clin. Microbiol 28(4):708–713, 1990.*
Glatman–Freedman et al, J. Clin. Microbiol 34(11):2795–2802, 1996.*
Mason et al, Tubercle & Lung Disease, 74:195–199, 1993.*
Bothamley, Eur. Respin. J.; 8, Suppl 20:6765–6885, 1995.*
Papa, et al., DOT–ELISA for detection of phenolic glycolipid PGL–Tb1 and diacyl–trehalose antigens of Mycobacterium tuberculosis, Res. Microbiol., 1992, 143. 327–331.
Mauch, et al., Monoclonal Antibodies Selectively Directed against the Cell Wall Surface of Mycobacterium Tuberculosis, J. Clin. Microbiol., 1988, 26(9), 1691–1694.
Wu, et al., Detection of Mycobacterial Antigens in Cerebrospinal Fluid by Enzyme–Linked Immunosorbent Assay Utilizing Anti–Mycobacterial Saline Extract Antibodies, Chinese J. Microbiol. Immunol. 1989. 22. 173–180.
Kolk, et al., Production and Characterization of Monoclonal Antibodies to Mycobacterium Tuberculosis, M. Bovis (BCG) and M. leprae, Clin. Exp. Immunol. 1984. 58. 511–521.
Friedman, et al., ELISA Analysis of BACTEC Bottles for the Earlier Diagnosis of Tuberculosis, American Review of Resp. Dis., 140(3):668–71, 1989.
Verstijnen, et al., Enzyme–Linked Immunosorbent Assay Using Monoclonal Antibodies for Identification of Mycobacteria from Early Cultures, J. Clin. Microbiol . . . 29(7). 1991. 1372–1375.
Kadival, et al., Sensitivity and Specificity of Enzyme–Linked Immunosorbent Assay in the Detection of Antigen in Tuberculosis Meningitis Cerebrospinal Fluids, J. Clin. Microbiol., 1986, 23(5); 901–904.
Cho, et al., Production of Monoclonal Antibodies to Lipoarabinomannan–B and use in the Detection of Mycobacterial Antigens in Sputum, Yonsei Medical Journal, 31(4), 1990, 333–338.

* cited by examiner

*Primary Examiner*—Patricia A. Duffy
(74) *Attorney, Agent, or Firm*—Amster, Rothstein & Ebenstein (57) ABSTRACT

The present invention provides for monoclonal antibodies, the hybridoma cell lines which produce these antibodies, and the use of such monoclonal antibodies in the detection of *M. tuberculosis*. More specifically, the present invention provides for monoclonal antibodies that react with surface epitopes of *M. tuberculosis* and the use of these monoclonal antibodies for detecting and diagnosing *M. tuberculosis*. Also provided by the present invention is a modified ELISA assay for detection of microorganisms, and a modified ELISA assay employing the monoclonal antibodies of the present invention for detecting *M. tuberculosis*.

12 Claims, 7 Drawing Sheets

MONOCLONAL ANTIBODIES TO *MYCOBACTERIUM TUBERCULOSIS* AND A MODIFIED ELISA ASSAY

STATEMENT OF GOVERNMENT INTEREST

This invention was made with government support under NIH Training Grant No. 1 T32 AI07501-01, and NIH Grant Nos. AI-33774 and AI-33142. As such, the government has certain rights in this invention.

BACKGROUND OF THE INVENTION

Tuberculosis continues to be a major worldwide health problem and is responsible for most incidences of death by an infectious agent. The worldwide incidence of tuberculosis was estimated by the World Health Organization to be 8.8 million in 1995, with a mortality estimate of 3.0 million persons, and is expected to rise to 10.2 million by the year 2000 (Dolin, et al., *Bull. WHO.* 72: 213–220 (1994)). The tuberculosis problem has been compounded by the development of the AIDS epidemic and the growing number of HIV-related cases of tuberculosis (Dolin, et al., *Bull. WHO.* 72: 213–220 (1994)).

As the incidence of tuberculosis increases, major problems also develop concerning this disease. For example, the lack of a sensitive and rapid laboratory method of diagnosing tuberculosis makes it difficult to differentiate between *M. tuberculosis* and *M. avium-intracellulare*, both of which are frequently present in HIV infected patients. Multiple methods of detection of *M. tuberculosis* employing polyclonal and monoclonal antibodies have been described (Cho, et al., *Yonsei Med. J.* 31:333–338 (1990); Cho, et al., *J. Clin. Microbiol.* 30: 3065–3069 (1992); Friedman, et al.,*Am. Rev. Respir. Dis.* 140: 668–671 (1989); Kadival, et al., *J. Clin. Microbiol.* 23: 901–904(1986); Mason, et al., *Tubercle Lung Dis.* 74:195–199(1993); Papa, et al., *Res. Microbiol.* 143: 327–331 (1992); Sada, et al., *Lancet* 2 651–652 (1983); Schoningh, et al., *J. Clin. Microbiol.* 28: 708–713 (1990); Verstijnen, et al., *J. Clin. Microbiol.* 29:1372–1375 (1991) Watt, et al., *J Infect Dis.* 158:681–686 (1988); Wu, et al., *Chin. J. Microbiol. Immunol.* 22:173–180 (1989); Yanez, et al., *Clin. Microbiol.* 23: 822–825 (1986)), but none have acquired a widespread role in the diagnosis of tuberculosis as these antibodies cross-react with other mycobacterial strains (Cho, et al., *Yonsei Med. J.* 31:333–338 (1990); Friedman, et al.,*Am. Rev. Respir. Dis.* 140: 668–671 (1989); Kadival, et al., *J. Clin. Microbiol.* 23: 901–904 (1986); Wu, et al., *Chin. J. Microbiol. Immunol.* 22:173–180 (1989); Yanez, et al., *J. Clin. Microbiol.* 23: 822–825 (1986)). In addition, in order to obtain significant results, a large amount of mycobacteria or mycobacterial antigen is required (Cho, et al., *J. Clin. Microbiol.* 30: 3065–3069 (1992); Mason, et al., *Tubercle Lung Dis.* 74:195–199 (1993); Papa, et al., *Res. Microbiol.* 143: 327–331 (1992); Schoningh, et al., *J. Clin. Microbiol.* 28: 708–713 (1990); Verstijnen, et al., *J. Clin. Microbiol.* 29:1372–1375 (1991)). Improvements in antibody-based diagnostic tests for the detection of *M. tuberculosis* would require specific antibody reagents with high affinity for mycobacterial antigens. Several monoclonal antibodies have been generated against surface components of *M. tuberculosis* (Cho, et al., *Yonsei Med. J.* 31:333–338 (1990); Cho, et al., *J. Clin. Microbiol.* 30: 3065–3069 (1992); Mauch, et al., *J. Clin. Microbiol.* 26:1691–1694 (1988)) but they are often cross reactive with other strains or cytoplasmic fractions (Cho, et al., *Yonsei Med. J.* 31:333–338 (1990); Mauch, et al., *J. Clin. Microbiol.* 26:1691–1694 (1988)). There is thus a need for a monoclonal antibody that selectively binds to *M. tuberculosis* and does not cross react with other strains of mycobacteria.

An additional problem concerns the protocol used for detecting *M. tuberculosis*. The protocols described thus far for detecting mycobacteria, such as direct ELISA (Mason, et al., *Tubercle Lung Dis.* 74:195–199 (1993); Schoningh, et al.,*J. Clin. Microbiol.* 28: 708–713 (1990); Verstijnen, et al., *J. Clin. Microbiol.* 29:1372–1375 (1991)), capture ELISA (Cho, et al., *Yonsei Med. J.* 31:333–338 (1990); Cho, et al., *J. Clin. Microbiol.* 30: 3065–3069 (1992); Friedman, et al., *Am. Rev. Respir. Dis.* 140: 668–671 (1989); Kadival, et al., *J. Clin. Microbiol.* 23: 901–904 (1986); Rattan, et al., *Tubercle Lung Dis.* 74: 200–203 (1993); Sada, et al., *Lancet* 2 651–652 (1983); Watt, et al., *J Infect Dis.* 158:681–686 (1988); Wu, et al., *Chin. J. Microbiol. Immunol.* 22:173–180 (1989); Yanez, et al., *J. Clin. Microbiol.* 23: 822–825 (1986)) and DOT ELISA (Cho, et al.,*J. Clin. Microbiol.* 30: 3065–3069 (1992); Papa, et al., *Res. Microbiol.* 143: 327–331 (1992)), are deficient in many areas. For example, none of the methods listed above allow for visualization of single captured microorganisms. Furthermore, many of these methods require the use of polyclonal immunoglobulins which have the potential disadvantages of lot to lot variation, reliance on animal sources and unwanted cross-reactivities. Accordingly, there is an outstanding need for a method of detecting *M. tuberculosis* which eliminates the problems existing in current methods of detection.

SUMMARY OF THE INVENTION

The present invention provides for monoclonal antibodies, the hybridoma cell lines which produce these antibodies, and the use of such monoclonal antibodies in the detection of *M. tuberculosis*. More specifically, the present invention provides for monoclonal antibodies that react with surface epitopes of *M. tuberculosis* and the use of these monoclonal antibodies for detecting and diagnosing *M. tuberculosis*.

Also provided by the present invention is a modified ELISA assay for detection of microorganisms, and a modified ELISA assay employing the monoclonal antibodies of the present invention for detecting *M. tuberculosis*.

BRIEF DESCRIPTION OF THE FIGURES

FIG. 1.

FIGS. 2A and 2B: FIG. 2 sets forth the double staining of *M. tuberculosis* by acid-fast staining and immunofluorescence (shown here as a clump) with monoclonal antibody 5c11 at a concentration of 10 μg/ml. FIG. 2B: Indirect immunofluorescence. Immunostaining with monoclonal antibodies 4f11 and 9d8 produced similar fluorescence (not shown). Bar, 10 μm. The picture was generated using Kodak RFS 2035 scanner and Adobe Photoshop version 3.0 for Macintosh.

FIGS. 3A, 3B and 3C: FIGS. 3A, 3B, and 3C correspond to monoclonal antibodies 5c11, 4f11 and 9d8 respectively. Bar=0.2 μm.

FIGS. 4A, 4B, and 4C.

Filled symbols correspond to monoclonal antibody binding to periodate treated mycobacteria whereas open symbols correspond to non-periodate treated mycobacteria. FIGS. 4A, 4B, and 4C correspond to monoclonal antibodies 5c11, 4f11 and 9d8, respectively. Diagram shows the ELISA configuration.

FIGS. 5A, 5B, and 5C: FIGS. 5A–5C show the binding of monoclonal antibodies at various concentrations to mycobacterial surface carbohydrates.

FIGS. 6A, 6B, and 6C: FIGS. 6A, 6B, and 6C correspond to monoclonal antibodies 5c11, 4f11 and 9d8, respectively. The diagram shows the ELISA configuration.

FIGS. 7A and 7B: FIGS. 7A and 7B sets forth the results of the modified ELISA spot assay.

DETAILED DESCRIPTION OF THE INVENTION

The present invention is directed to novel monoclonal antibodies immunoreactive with cell surface antigens of M. tuberculosis, the hybridoma cell lines which produce these antibodies, and methods of detecting M. tuberculosis.

The hybridoma cell lines provided by the present invention were obtained by immunizing mice with whole cells of M. tuberculosis* using methods commonly know to those skilled in the art. Spleen cells were obtained from mice exhibiting a positive antibody reaction and fused with myeloma cells to obtain hybridoma cells which secrete monoclonal antibodies against the cell wall of *M. tuberculosis*. The hybridoma cell lines which secret these antibodies are herein designated H-4f11, H-5c11, and H-9d8. H-9d8 has been deposited in the American Type Culture Collection (ATCC), 10801 University Blvd., Manassas, Va. 20110-2209 on Jun. 3, 1997, under ATCC Accession Number HB 12364. This deposit was made pursuant to and in satisfaction of the Budapest Treaty on the International Recognition of the Deposit of Microorganisms for the Purposes of Patent Procedure. The hybridoma cell lines provided by the present invention may be fused with other cells to transfer the genes which express the monoclonal antibodies, thus providing new hybridomas.

The monoclonal antibodies generated by these hybridoma cell lines are herein designated 4f11, 5c11, and 9d8. These antibodies were characterized by ELISA, indirect immunofluorescence and immunoelectronmicroscopy. The antibodies, however, may be purified by any convenient techniques, such as chromatography, electrophoresis, precipitation, and extraction. Monoclonal antibody 4f11 recognizes a cell wall carbohydrate that belongs to the mycolyl-arabinogalactanpeptidoglycan (mAGP) complex of mycobacteria, monoclonal antibody 5c11 binds lipoarabinomannan (LAM), and monoclonal antibody 9d8 selectively binds to a non-protein cell surface epitope of *M. tuberculosis.*

The monoclonal antibodies of the present invention may be employed without further change, or may be reduced to various sized fragments. The monoclonal antibodies described herein may be labeled with cytotoxic agents, antibiotics, and standard detectable markers, such as chemiluminescent detection systems, radioactive labels such as $^{125}$I, and enzymes such as horseradish peroxidase, biotin, and avidin.

The monoclonal antibodies of the present invention may be presented in kits with detectable labels and other reagents and buffers for such detection. For example, monoclonal antibody 9d8 may be presented as part of a serological reagent for identification of *M. tuberculosis*. The labeled antibodies presented in the kits may be labeled with any standard detectable markers, such as chemiluminescent detection systems, radioactive labels such as $^{125}$I, and enzymes such as horseradish peroxidase, biotin, and avidin.

The monoclonal antibodies of the present invention may be employed in the diagnosis and detection of *M. tuberculosis* in clinical samples such as body fluids and cell culture. Non-limiting examples of clinical samples that may assessed by the methods of the present invention are sputum, cerebrospinal fluid, blood, serum, plasma, mucus, urine, feces, cell culture, and any mixture thereof.

The present invention also provides a method for detecting the presence of *M. tuberculosis* in a subject, comprising the use of monoclonal antibody 9d8. This method is useful for diagnosing tuberculosis in a subject. *M. tuberculosis* may be detected using monoclonal antibody 9d8 by procedures known in the art including, but not limited to, immunoblotting, immunoprecipitation, solid phase radioimmunoassay (e.g. competition RIAs, immobilized antigen or antibody RIAs, or double antibody RIAs), enzyme-linked immunoabsorbant assay, and the like. The monoclonal antibody may also be conjugated to radioactive isotope and the individual scanned for the presence of *M. tuberculosis.*

In a preferred embodiment of the invention, the method for detecting *M. tuberculosis* in a sample or a subject employs two antibodies in an ELISA assay. For example, the ELISA assay may employ monoclonal antibody 5c11 as a "capture" antibody. Since all mycobacteria possess LAM on their cell surfaces, 5c11 would bind the cell surfaces of all mycobacteria and effectively "capture" the mycobacteria. The ELISA assay may also employ monoclonal antibody 9d8, which would "select" *M. tuberculosis* for binding from all other species of mycobacteria.

In a specific embodiment of the invention, monoclonal antibodies 5c11 and 9d8 are used in an ELISA assay to differentiate between *M. tuberculosis* and *M. avium-intracellular* in a subject. As monoclonal antibody 9d8 selectively binds to *M. tuberculosis,* one may effectively rule out infection caused by *M. avium-intracellulare* in a subject where both *M. tuberculosis* and *M. avium-intracellulare* may be equally prevalent, such as in HIV infected subjects. The subject may be diagnosed using the 9d8 monoclonal antibody of the present invention in an immunoassay as described above, or by an ELISA assay using both monoclonal antibodies 5c11 and 9d8. Other methods for using the monoclonal antibodies described herein are discussed in U.S. application Ser. No. 08/868,545 filed Jun. 4, 1997, entitled "Methods of Treating and Protecting Against Tuberculosis Using a Monoclonal Antibody Selective for Mycobacterium Tuberculosis", which is herein incorporated by reference.

In addition to providing monoclonal antibodies to *M. tuberculosis* and uses of these antibodies in the detection and diagnosis of *M. tuberculosis*, the present invention also provides a novel modified ELISA assay which solves the problems posed by immonoassays currently used. The modified ELISA assay provided by the present invention employs a "capture" method of detection, using two monoclonal antibodies that do not compete for binding on the cell surface of the microorganism. Specifically, the modified ELISA capture method provided herein comprises contacting a surface with a monoclonal antibody that recognizes an epitope of the microorganism to be detected. In a preferred embodiment of the invention, the surface is polystyrene, and is in the form of a slide chamber with removable cell walls. In this case, the chambers are coated with unlabeled goat anti-mouse IgM specific antibody, blocked with BSA, and washed. The "capture" monoclonal antibody is then added. The "capture" monoclonal antibody must bind to an epitope on the surface of the microorganism to be detected. In a preferred embodiment of the invention, monoclonal antibody 5c 11 is used which binds to a cell surface lipopolysaccharide, lipoarabinomannan, that is common to all mycobacteria, and thus and "captures" all mycobacteria.

Examples of microorganisms that may be detected using the modified ELISA assay of the present invention include, but are not limited to, *M. tuberculosis, M. gastri, M. kansasii,* and *M. gordonae*.

The next step of the modified ELISA assay comprises addition of a sample preparation to the chamber. The sample preparation is usually a clinical sample such as a body fluid or a cell culture. Non-limiting examples of clinical samples that may assessed by the modified ELISA assay aare sputum, cerebrospinal fluid, blood, serum, plasma, mucus, urine, feces, cell culture, and any mixture thereof. After washing, the second monoclonal antibody is added. This antibody preferably is selective for the microorganism to be detected, and binds to a different epitope on the cell surface of the microorganism than the "capture" monoclonal antibody. In a preferred embodiment of the invention, the selective monoclonal antibody used is 9d8, and binds selectively to *M. tuberculosis*. After incubation, the excess antibody is removed by washing, and a labeled antibody is added which will bind to the remaining selective monoclonal antibodies which are presumably bound to the microorganism to be detected. The label may be a detectable marker. Examples of detectable markers include, but are not limited to, chemiluminescent detection systems, radioactive labels such as $^{125}$I, enzymes such as horseradish peroxidase, biotin, and avidin.

After incubation and washing, the chamber is contacted with a stain, then a non-soluble color developer. Examples of non-soluble color developers which may be used include those that are chromogenic and those that are luminescent. Examples of chromogenic color developers include the horseradish peroxidase based, such as 3-amino-9-ethycarbazole (AEC), 4-chloro-1-napthol (4CN), 3-3'-diaminobenzidine (DAB/NiCl$_2$), 2,2'-azino-bis(3-ethylbenzthiazoline-6-sulfonic acid) (ABTS) and 3,3',5,5'-tetramethylbenzadine (TMB); and the alkaline phosphatase based, such as bromo-4-chloro-3-indolyl phosphate (BCIP). Examples of luminescent systems include luminol/H$_2$O$_2$/p-iodophenol, and substituted 1,2-dioxetane-phosphates, such as AMPPD, CSPD, Lumigen-PPD, and Lumi-Phos 530. The non-soluble color developer is then removed and the surface is allowed to dry. For viewing of the stained cells, the chamber walls are removed, leaving a slide. The removal of the chamber walls allows for direct microscopic viewing of the stained microorganisms. In one embodiment of the invention, the preferred manner of viewing a microorganism is by light microscopy. The removal of the chamber walls also allows for the direct viewing of very small microorganisms, such as mycobacteria, as the 100× magnification lens may be positioned very close to the surface of the slide. In a preferred embodiment of the invention, the modified ELISA capture method employs the monoclonal antibodies 5c11 and 9d8 of the present invention for the detection of *M. tuberculosis*.

The present invention is described in the following Experimental Details Section, which is set forth to aid in an understanding of the invention, and should not be construed to limit in any way the invention as defined in the claims which follow thereafter.

Experimental Details Section

A. Materials and Methods

*M. tuberculosis* for immunization and hybridoma testing. *M. tuberculosis* Erdman strain was obtained from Trudeau Mycobacterial Culture Collection, Trudeau Institute, Saranac Lake, N.Y. (TMC 107) and grown in Proskauer-Beck-Trudeau (PBT) medium without Tween at 37° C. for 5 weeks. Mycobacterial cells were washed twice in phosphate-buffered-saline (PBS), heat inactivated at 80° C. for 2 h and sonicated for 3 to 5 seconds (Branson Ultrasonics, Danbury, Conn.).

Mycobacterial strains for cross reactivity testing. Mycobacterial strains used in this study originated from the American Type Culture Collection, —Manassas, Va. (ATCC), Trudeau Mycobacterial Culture Collection, Trudeau Institute, Saranac Lake, N.Y. (TMC), Centers for Disease Control, Atlanta, Ga. (CDC), NY Department of Health (NY DOH), P. D'Arcy Hart (PDH) and College of American Pathologists, Northfield, Ill. (CAP). *M. tuberculosis* (TMC 107), *M.bovis*-BCG (Pasteur Institute), *M. Microti* (PDH), *M. avium* (CAP—Inderlied 101), *M. smegmatis* (CDC), *M. xenopi* (ATCC 19250), *M. chitae* (ATCC 19627), *M. marinum* (ATCC 927), *M. chelonae* (CDC), *M. gastri* (ATCC 25028), *M. kansasii* (ATCC 12478), *M. vaccae* (CDC), *M. phlei* (TMC 1516), *M. fortuitum* (ATCC 6841), *M. terrae* (ATCC 15755), *M. szulgai* (ATCC 35799) and *M. gordonae* (ATCC 14470) were grown in Lowenstein-Jensen (LJ) slants. Several bacterial species were obtained as well: *Streptococcus pneumoniae, Escherichia coli, Corynebacterium pseudodiphtheria, seudomonas aeruginosa, Haemophilus influenzae* (quality control strains obtained from the Clinical Microbiology Laboratory, Montefiore Medical Center, Bronx, N.Y.) and *Nocardia asteroides* (clinical isolate, Mycology Laboratory, Montefiore Medical Center, Bronx, N.Y.). Cells were obtained from the media surface using a sterile loop, suspended in PBS with 0.1 mM sodium azide, sonicated briefly as described above to break clumps (when needed) and heat treated at 80° C. for 2 h.

*M. tuberculosis* Whole Cell ELISA. A 50 $\mu$l suspension of 1–2×10$^7$ *M. tuberculosis* suspended in phosphate-buffered-saline (PBS) pH 7.2 was placed in microtiter ELISA plate wells and incubated at room temperature for 2 h. Prior to use in ELISA the *M. tuberculosis* suspension was briefly sonicated as described above. Plates were blocked with 1% bovine serum albumin (BSA) and 0.05% horse serum in PBS and stored at 4° C. Plates were washed 3 times with 0.05% Tween 20 in PBS. Hybridoma cell supernatants containing monoclonal antibodies were added to each well and the plates were incubated 1–1.5 h at 37° C. or overnight at 4° C. Plates were then washed 3 times, and 1 $\mu$g/ml goat anti-mouse alkaline phosphatase conjugated antibody (Southern Biotechnology Associates, Inc. Birmingham, Ala.) was added to each well and incubated 1–1.5 h at 37° C. After washing 5 times, a solution of 1 mg/ml p-nitrophenyl phosphate (Southern Biotechnology Associates, Inc. Birmingham, Ala.) in substrate buffer (0.001 M $MgCl_2$, 0.05 M $Na_2CO_3$, pH 9.8) was added (50 µl/well) and absorbance was measured at 405 nm in a Ceres 900 HDi reader (Bio-Tek Instruments Inc. Winooski, Vt.). ELISA measurements were the average of 3 microtiter wells.

Immunization. Balb/c mice (Jackson Laboratories, Bar Harbor, Me.) were injected intraperitoneally (i.p.) with approximately $2\times10^9$ M. tuberculosis Erdman strain in an emulsion with incomplete Freund adjuvant (0.2 ml per mouse). The mice were boosted every 12–18 d for a period of seven weeks with $4.4\times10^7$ to $1\times10^9$ organism. Several booster injections included incomplete Freund adjuvant. Serum was examined for antibodies to M. tuberculosis by whole cell ELISA, and the mouse with the highest titer rise was boosted 4 d prior to fusion using $1\times10^9$ organisms in Incomplete Freund's Adjuvant.

Fusion. Spleen cells were harvested on day 50, fused with NSO myeloma cells at a ratio of 4:1 and suspended in HAT media. A total of 12 plates were seeded with fusion products and incubated at 37° C. with 10% $CO_2$. Hybridoma supernatants were screened for antibody production by whole cell ELISA.

Indirect Immunofluorescence (IF). This method was adapted from Jones et al. 1964 (Jones, et al., *Am. Rev. Respir. Dis.* 92: 255–260 (1965)). Approximately $1\times10^7$ heat killed M. tuberculosis were placed on a poly-L-lysine coated glass microscope slide (Poly-Prep slides, Sigma Diagnostics, St. Louis, Mo.) and fixed by heating at 65° C. for 2 h. Primary antibody was added at concentrations of 10, 1, 0.1, 0.01, 0.01 µg/ml, and the slides were incubated for 30 min at room temperature. The slides were then washed with distilled water and incubated with FITC labeled anti mouse IgM or IgG (Southern Biotechnology Associates, Inc. Birmingham, Ala.) at a concentration of 10 µg/ml for 30 minutes at room temperature, without light. The slides were washed again with distilled water and sealed with mounting media (1.4 g glycine, 0.07 g NaOH, 1.7 g NaCl, 0.1 g sodium azide in 100 ml of distilled water, pH 8.6) with 1% n-propyl gallate. As a positive control, separate slides with M. tuberculosis cells were stained with acid-fast staining prior to indirect immunofluorescence. Negative controls consisted of *Cryptococcus neoformans* cells incubated with anti-M. tuberculosis antibodies, and M. tuberculosis incubated with anticryptococcal monoclonal antibodies of the same isotype. An additional negative control consisted of incubation of M. tuberculosis with FITC labeled antibodies.

Immunoelectronmicroscopy. A small pellet of heat killed M. tuberculosis was incubated in a microcentrifuge tube with 10 µg/ml monoclonal antibody in 1% BSA in PBS for 1 h at room temperature in a slow shaking motion. Cells were washed twice with PBS and incubated with gold labeled goat anti-mouse IgM+IgG (Amersham Life Science, Buckinghamshire, England), and diluted 1:30 in 1% BSA in PBS using the same conditions as above. Cells were then washed and fixed in Trump's fixative solution (4% paraformaldehyde and 1% glutaraldehyde in 0.1 M phosphate buffer at pH 7.3) overnight. Post fixation was done with 2% osmium for 1 h. Afterwards the cells were washed in 0.1 M phosphate buffer (pH 7.3) and dehydrated by incubation in solutions with increasing ethanol concentrations (10 min each in 50, 70, 80, 95% ethanol, followed by two 15 min dehydration in 100% ethanol) and two 10 min dehydrations in acetonitrile. The cell pellet was then infiltrated with 1:1 acetonitrile:araldite-epon overnight followed by 2 changes of aralide-epon and incubated overnight at room temperature. The blocks were polymerized for 2 d at 65° C. Thick sections were stained with toluidine blue, and thin sections were stained with 3% uranyl acetate in 30% ethanol for 15 min and by lead citrate for 2 min. The sections were examined in a JEOL 100CX or 100S electron microscope.

Epitope Chemical Analysis ELISAs. Several ELISA's were used to determine the nature of the epitopes recognized by the monoclonal antibodies. Whole cell M. tuberculosis was initially used which were treated with Sodium meta-periodate or Proteinase K. The protocol for Sodium meta-periodate ELISA was adapted from the method of Udaykumar & Saxena (Udaykumar, and R. K. Saxena. *Microbiol. Immunol.* 76: 7–12 (1991)). A 50 µl volume containing $1-2\times10^7$ M. tuberculosis suspended in PBS was incubated in a microtiter polystyrene plate wells for 2 h at room temperature. After M. tuberculosis attached to the plate, the supernatant was removed and 50 µl of 0.1 M sodium meta-periodate (Sigma Chemical Co. St. Louis, Mo.) in 0.1 M acetate buffer (pH 4.5) was added to each well. Control wells had buffer only. The plates were incubated for 2 h at 4° C. in the dark, washed 5 times with 0.05% Tween 20 in PBS, and blocked with 200 µl 1% BSA in PBS. The plates were then used in ELISA to determine antibody binding to periodate treated M. tuberculosis. A similar ELISA procedure was done employing Proteinase K (Boehringer Manheim GmbH, Manheim, Germany) instead of sodium meta-periodate. Briefly, the plates were incubated with 100 µl of proteinase K at a concentration of 1 mg/ml in PBS or with PBS alone (as a control) at room temperature for 20 h and used as before.

ELISA was used to determine monoclonal antibody binding to mycobacterial fractions. Total lipid fraction (TLF) lipoarabinomannan (LAM), lipomannan (LM), mycolyl-arabinogalactan-peptidoglycan complex (mAGP—with protein contamination of 34 ng/mg) and phosphatidylinositol mannoside (PIM) from M. tuberculosis Erdman strain was kindly supplied by P. J. Brennan and J. T. Belisle (Department of Microbiology, Colorado State University, Fort Collins). The fractions were prepared from M. tuberculosis strain Erdman, except for LM which was prepared from fast growing Mycobacterium sp.

The TLF ELISA used is a modification of protocols described previously (Cho, et al., *J. Clin. Microbiol.* 30: 3065–3069 (1992)). TLF was suspended in 100% ethanol, added to polystyrene microtiter plates, serially diluted starting at a concentration of 1 mg/ml, and air dried overnight. The plates were then blocked with a solution of 1% BSA in PBS with 0.05% horse serum for 1.5 h at 37° C. and used to study monoclonal antibody binding to total lipid fraction by ELISA. Wells incubated with 100% ethanol without lipid antigen served as negative controls.

For the mycobacterial carbohydrate fraction ELISAs, a suspension of 100 µl mycobacterial antigens dissolved in carbonate buffer (pH 9.6) was placed in microtiter ELISA wells and incubated overnight at 4° C. (The concentrations of antigens LAM and mAGP were 10 µg/ml and 1 mg/ml respectively. LM and PIM were placed in serial dilutions starting at 50 µg/ml). Plates were then blocked with 3% BSA in PBS for 1.5 h at 37° C. After washing, 50 µl monoclonal antibodies solution (serial dilutions starting at 10 µg/ml for LAM and mAGP ELISAs and fixed concentration of 10 µg/ml for PIM and LM ELISAs) were added and ELISA procedure was followed as above. For comparative LAM-versus-LM ELISA 100 µl of antigen solution at 1 µg/ml were suspended in carbonate buffer (pH-9.6) and placed in microtiter ELISA plates. A 50 µl volume of relevant monoclonal antibody (5c11) was serially diluted across a microtiter plate starting at 10 µg/ml and the procedure was followed as above. Wells containing 50 μl carbonate buffer without antigen served as a control.

Western blot analysis. Whole cell *M. tuberculosis* Erdman strain were suspended in RIPA buffer (50 mM Tris Cl pH 7.5, 150 mM NaCl, 1% Nonidet P-40, 0.5% sodium deoxycholate, 0.1% SDS), frozen at −70° C., thawn, sonicated for 10 min and analyzed by sodium dodecyl sulfate polyacrylamide gel electrophoresis (SDS-PAGE) before and after reduction with β-mercaptoethanol in 12% gels. Gels were blotted onto nitrocellulose sheet and non specific binding sites were blocked with 3% gelatin in Tris buffered saline pH 7.5 (TBS) (BIO-RAD Laboratories, Hercules, Calif.). Blots were incubated overnight with either 10 μg/ml or 50 μg/ml monoclonal antibody diluted with 1% gelatin in 0.05% Tween in TBS (TTBS) at room temperature. After primary antibody incubation the blots were incubated with goat anti-mouse horseradish peroxidase-conjugated secondary antibody solution (BIO-RAD Laboratories, Hercules, Calif.) diluted 1:30 in 1% gelatin (BIO-RAD Laboratories, Hercules, Calif.). The blots were developed using color development reagents (BIO-RAD Laboratories, Hercules, Calif.) until the appearance of brown color. The positive control was an IgG1 monoclonal antibody to the 70 kD heat shock protein of *M. tuberculosis*.

Binding to other mycobacterial and bacterial strains. Comparative binding to other mycobacterial strains was done by whole cell ELISA and indirect immunofluorescence. Cells of mycobacterial and non-mycobacterial strains were suspended in PBS with 0.01 M sodium azide and washed twice. For whole cell ELISA mycobacterial and bacterial cells were resuspended to a turbidity value of 1 McFarland, placed in microtiter polystyrene plate and incubated overnight at 4° C. Plates were then blocked with 1% BSA in PBS with 0.05% horse serum 1.5 h at 37° C. After washing, a 50 μl of monoclonal antibodies solution at 5 μg/ml was added, and the ELISA procedure was followed as described above.

For comparative indirect immunofluorescence, the cells of mycobacterial strains were suspended in PBS with 0.01 M sodium azide and washed twice with PBS. In addition to the standard strains, 3 clinical isolates of *M. tuberculosis* grown on LJ slants were tested. A 50 μl volume of a mycobacterial suspensions was placed on a poly-L-Lysine coated glass microscope slides (Poly-Prep slides, Sigma Diagnostics, St. Louis Mo.) and fixed by heating at 65° C. for 2 h. The immunofluorescence protocol was performed as described above using primary antibody at a concentration of 5 μg/ml and secondary FITC-labeled antibody at a concentration of 10 μg/ml. Negative controls consisted of incubating the various mycobacterial strains with FITC-labeled antibodies. The presence of mycobacteria on the slides was verified by acid-fast staining (performed on a separate slide).

Capture ELISA Spot Assay. This ELISA was adapted from Spira, et al (Spira, G., and M. D. Scharff M. *J. Immunol. Methods* 148:121–129 (1992)), for the purpose of capturing and visualizing single mycobacteria. A slide chamber (developed by NUNC, Inc. Naperville, Ill. as a research and development product) was used. The slide chamber combines qualities of an ELISA plate and a microscope slide. The slide chamber is made of a Maxi-sorp treated polystyrene slide with removable 800 μl volume chambers attached. The chambers were coated with 200 μl unlabeled goat anti-mouse IgM specific antibody by incubating a 10 μg/ml solution for 1.5 h at 37° C. and blocked for non-specific binding by adding 400 μl of 2% BSA in PBS and incubating at 37° C. for 1.5 hours. Chambers were washed 3 times with 0.05% Tween 20 in PBS. Monoclonal antibody 5c11 (IgM) at a concentration of 10 μg/ml in PBS was then added and incubated at 37° C. for 1.5 h followed by washing with 0.05% Tween 20 in PBS. A sample preparation, consisting of heat killed *M. tuberculosis* Erdman strain mixed with mice serum was incubated overnight at 4° C. Chambers were washed 3 times and 5 μg/ml of monoclonal antibody 9d8 (IgG3) was added. Chambers were incubated for 1 h at 37° C., washed as before and incubated with 1 μg/ml Biotin labeled IgG3 (Southern Biotechnology Associates, Inc. Birmingham, Ala.) for 1 h at 37° C. After washing, a 200 μl volume of Vectastatin ABC-AP (standard kit) (VECTOR Laboratories, Burlingame Calif.) were added, and the chambers were incubated at room temperature for 30 min. After 5 wash cycles, staining was performed by adding 200 μl of 1 mg/ml bromo-4-chloro-3-indolyl phosphate (BCIP) (Amersco, Solon, Ohio) diluted in AMP buffer. After 1 h the chambers were washed with distilled water and air dried. The chamber walls were removed, a cover slide was placed, and the slide was observed under light microscopy at 100×magnification for mycobacteria which were stained blue.

Comparative binding of monoclonal antibody 9d8 to clinical strains of *M. tuberculosis* and *M. avium-intracellulare* complex.

Materials: 5 clinical isolates of *M. tuberculosis* grown on 7H10 solid media; 5 clinical isolates of mycobacterium avium-intracellular complex (MAC) grown on 7H10 solid media; *M. tuberculosis* ERDMAN strain grown in PBT medium (control strain); glass slides; PBS with azide; Monoclonal antibody 9d8; and FITC-labeled anti-mouse IgG.

Methods: Preparation of samples: Organisms were removed from medium with a sterile loop and suspended in 5 ml PBS with azide and washed. 3 drops (approximately 100 μl) were placed on a glass slide and fixed overnight at 70° C. Staining: Indirect immunofluorescence using 9d8. Staining was performed as described above, but not as a double stain. Positive controls: (1) Acid-fast stains of all strains performed in parallel to the experiment. (2) IF of *M. tuberculosis* ERDMAN strain grown in PBT medium (standard strain). Negative control: IF using FITC labeled IgG only.

Results: As shown in Table 1 below, 9d8 binds all clinical strains of *M. tuberculosis;* it does not bind 4 out of 5 MAC clinical strains. The IF of the 5th MAC was undetermined, and there was high background fluorescence not allowing a clear result. The presence of mycobacteria on the slide was determined by acid-fast stain performed in parallel.

TABLE 1

| Mycobacteria | Acid-Fast | IF |
|---|---|---|
| *M. tuberculosis*-1 | + | + |
| *M. tuberculosis*-2 | + | + |
| *M. tuberculosis*-3 | + | + |
| *M. tuberculosis*-4 | + | + |
| *M. tuberculosis*-5 | + | + |
| *M. tuberculosis*-ERDMAN | | + |
| *M. tuberculosis*-FITC | | − |
| MAC-A | + | − |
| MAC-B | + | − |
| MAC-C | + | − |
| MAC-D | + | − |
| MAC-E | + | UD * |
| MAC-FITC | | − |

* UD - undetermined
MAC - Mycobacterium avium-intracellular complex

B. Results and Discussion

Isolation of hybridomas producing anti-*M. tuberculosis* antibodies. A single fusion was performed using the spleen from the mouse that raised the highest antibody titer against whole cell *M. tuberculosis* (titer was 2187 fold over background, prior to last boosting). A total of 1152 wells were seeded with fused NSO-myeloma-splenocytes and their supernatants were screened by whole cell *M. tuberculosis* ELISA 8 d after fusion. A total of 25 wells had optical density of >0.4 at 405 nm. After 2 cloning procedures in soft agar 3 stable clones (5c11, 9d8 and 4f11) were obtained. Isotype determination by ELISA with goat anti-mouse isotype specific reagents revealed that one clone (9d8) secreted IgG3 and two clones (5c11 and 4f11) secreted IgM. All 3 monoclonal antibodies had kappa isotype light chain.

Figure 1:
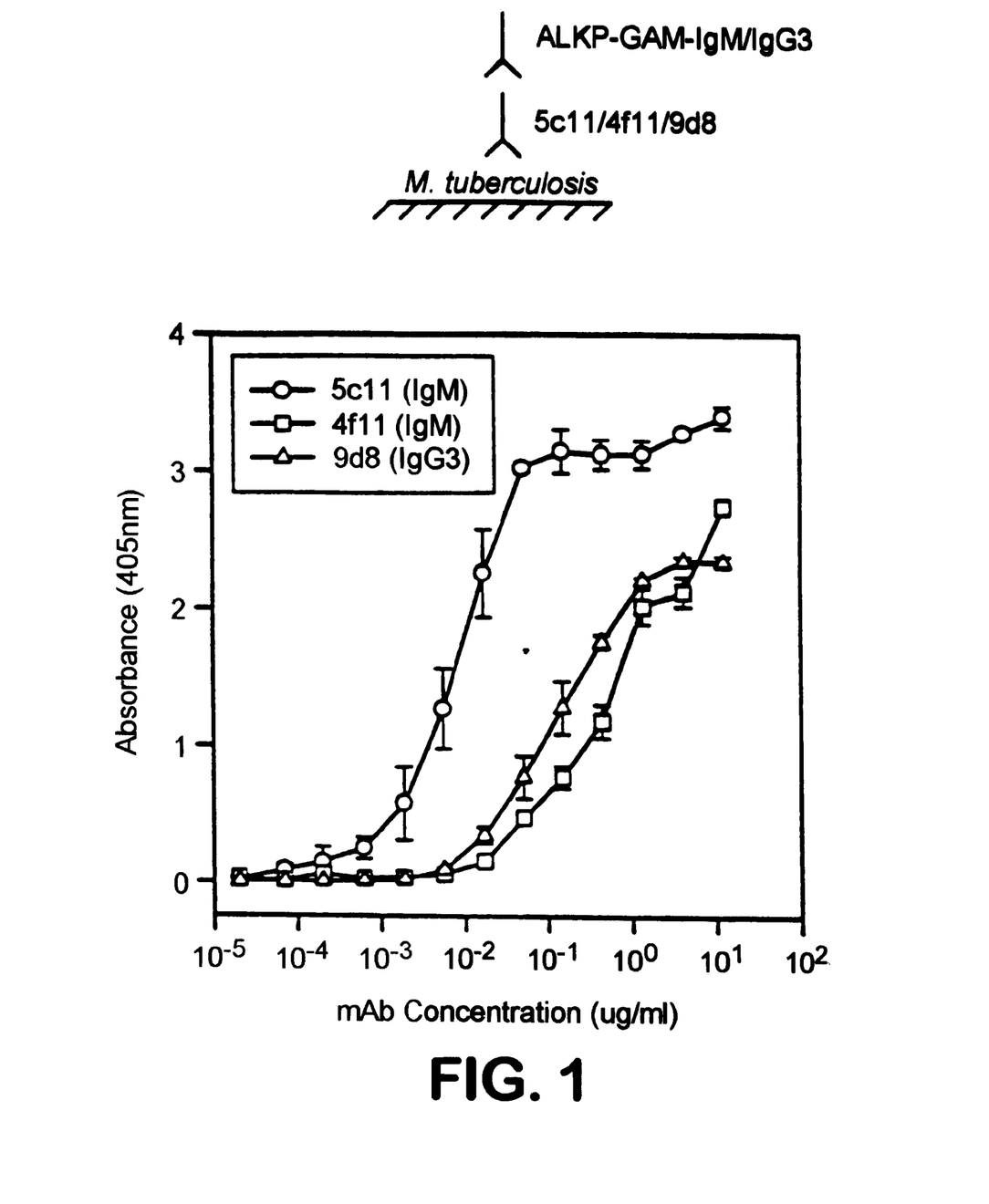
FIG. 1 sets forth the binding of monoclonal antibodies 5c11, 4f11, and 9d8 to *M. tuberculosis* whole cell ELISA at various concentrations. The diagram shows ELISA configuration.

*M. tuberculosis* whole Cell ELISA. All 3 monoclonal antibodies bound to plates coated with whole *M. tuberculosis* by ELISA. Comparative binding of the 3 monoclonal antibodies was performed by serially diluting the monoclonal antibodies. The binding curves show that monoclonal antibody 5c11 (IgM) required 10 to 15 times lower concentration than monoclonal antibodies 4f11 (IgM) or 9d8 (IgG3) to achieve the same optical density signal (FIG. 1). This difference was maintained even at very low optical density signals. This suggests either a higher binding affinity for 5c11 or a higher prevalence of 5c11 epitopes on the surface of *M. tuberculosis*.

Figure 2A:
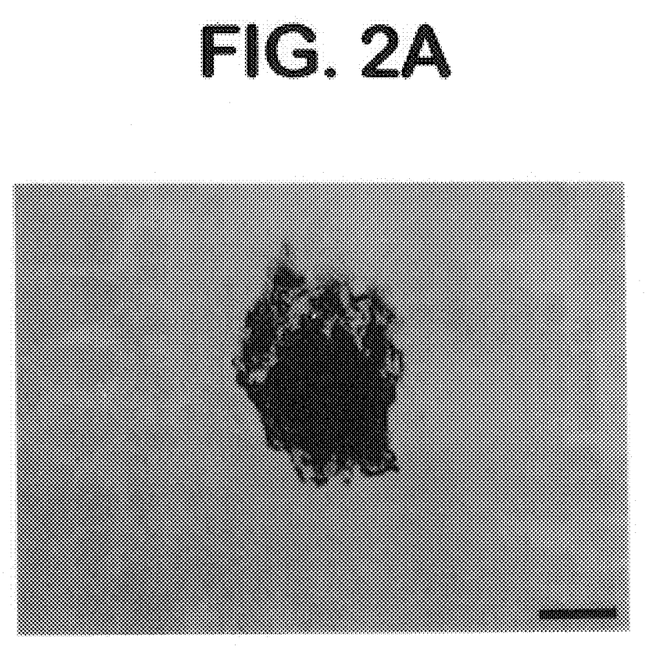
FIG. 2A: Acid-fast staining.
Figure 2B:
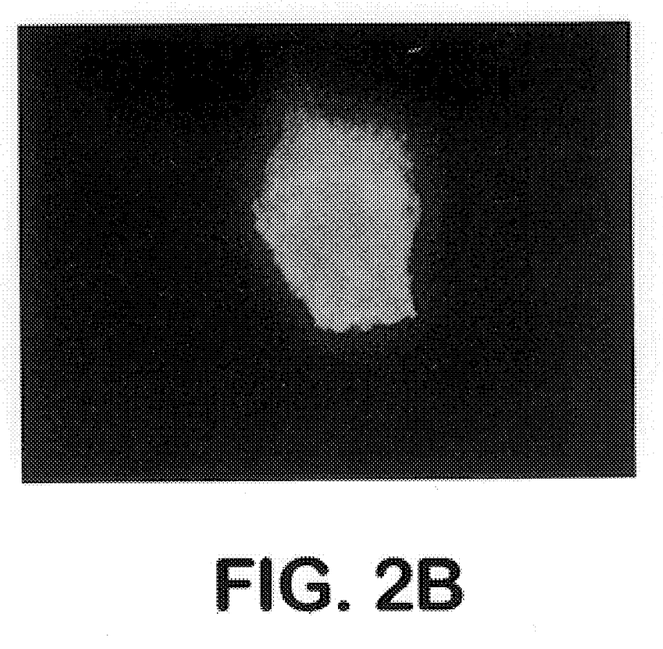

Indirect Immunofluorescence. All 3 monoclonal antibodies showed strong indirect immunofluorescence after incubation with whole cell *M. tuberculosis*. The fluorescence intensity was strongest at monoclonal antibody concentrations of 1–10 µg/ml and faded at monoclonal antibody concentration between 0.1 and 0.01 µg/ml (Table 2). An acid-fast staining prior to the addition of monoclonal antibodies and FITC conjugated antibodies, had little or no effect on the fluorescence intensity (FIG. 2).

TABLE 2

Immunofluorescence endpoints demonstrating signal intensity at various monoclonal antibody concentrations

|  | 10 µg/ml | 1 µg/ml | 0.1 µg/ml | 0.01 µg/ml | 0.001 µg/ml |
|---|---|---|---|---|---|
| 5c11 (IgM) | +++ | ++ | +$_w$ | − | − |
| 4f11 (IgM) | ++ | ++ | +$_w$ | − | − |
| 9d8 (IgG3) | +++ | ++ | + | − | − |

$_w$-weak

Figure 3A:
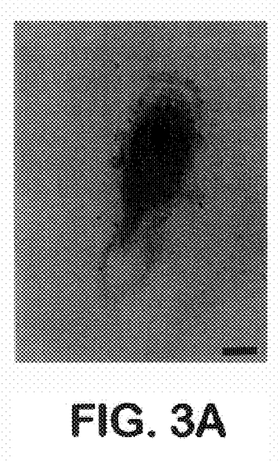
FIGS. 3A–3C represent immuno-electronmicroscopy demonstrating the binding of monoclonal antibodies to *M. tuberculosis*. Gold particles denote secondary antibody binding to the primary monoclonal antibody.
Figure 3B:
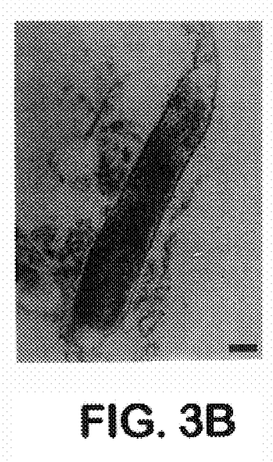
Figure 3C:
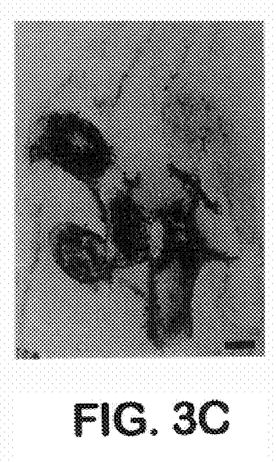

Immunoelectronmicroscopy. The binding of each monoclonal antibody to *M. tuberculosis* was studied by immunoelectronmicroscopy. Mycobacterial cell wall architecture was preserved but cytoplasmic mycobacterial structures could not be clearly identified due to the prolonged heat killing. Gold particles appeared to concentrate on the surface of the organism at or outside the level of the outer layer for each of the 3 monoclonal antibodies specimens (FIG. 3). Localization of gold particles to cell wall structures is consistent with the results of whole cell ELISA and immunofluorescence.

Figure 4A:
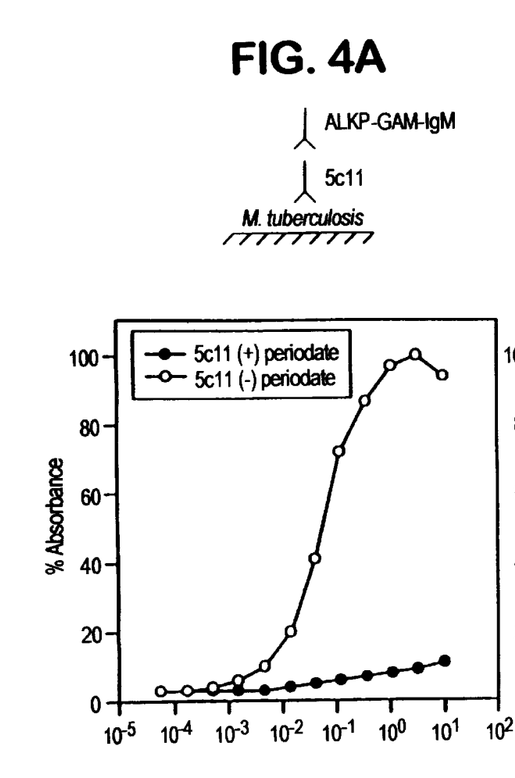
FIGS. 4A–4C show the binding of monoclonal antibodies 5c11, 4f11 and 9d8 with and without sodium meta-periodate treatment by whole cell ELISA.
Figure 4B:
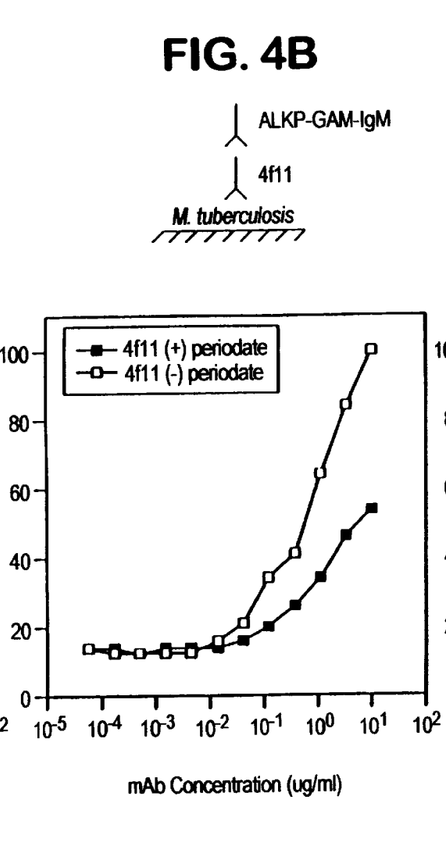
Figure 4C:
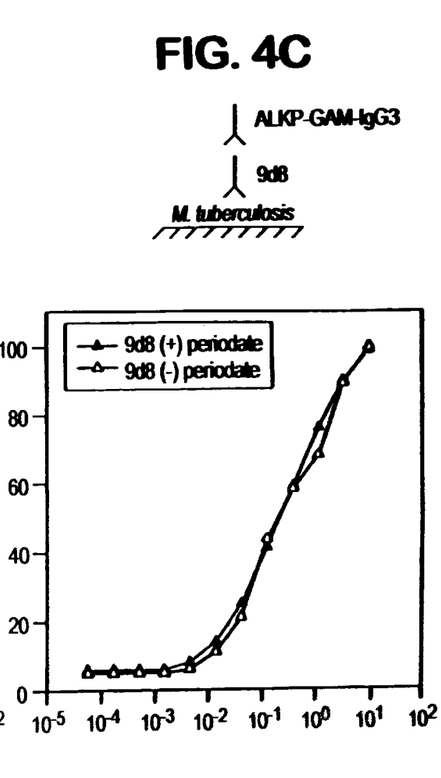
Figure 5A:
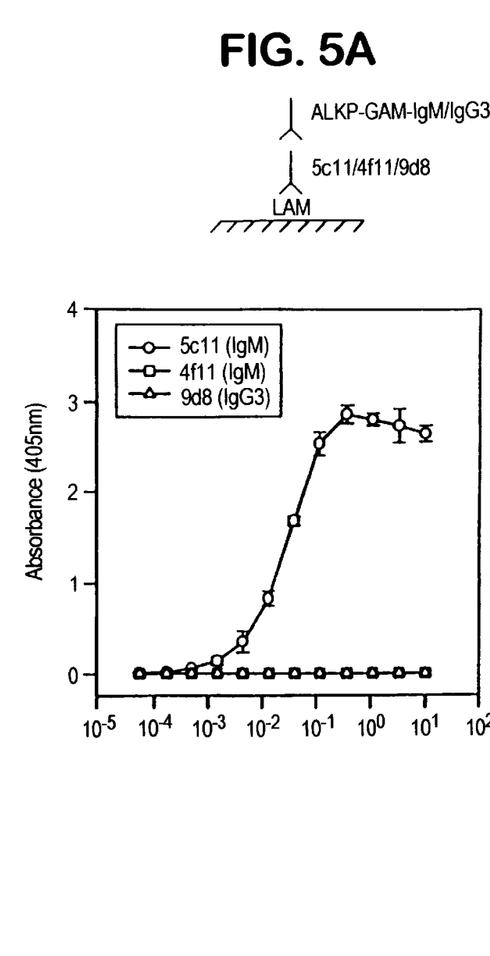
FIG. 5A: Binding of 5c11, 4f11 and 9d8 to LAM.
Figure 5B:
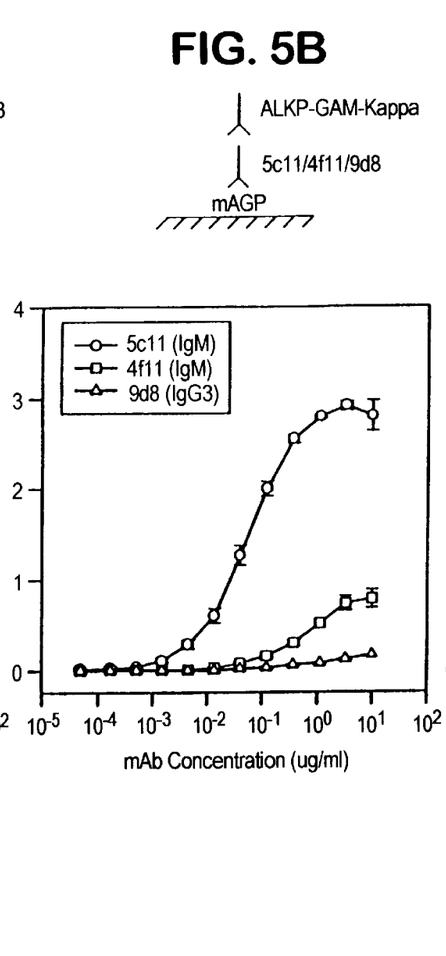
FIG. 5B: Binding of 5c11, 4f11 and 9d8 to mAGP.
Figure 5C:
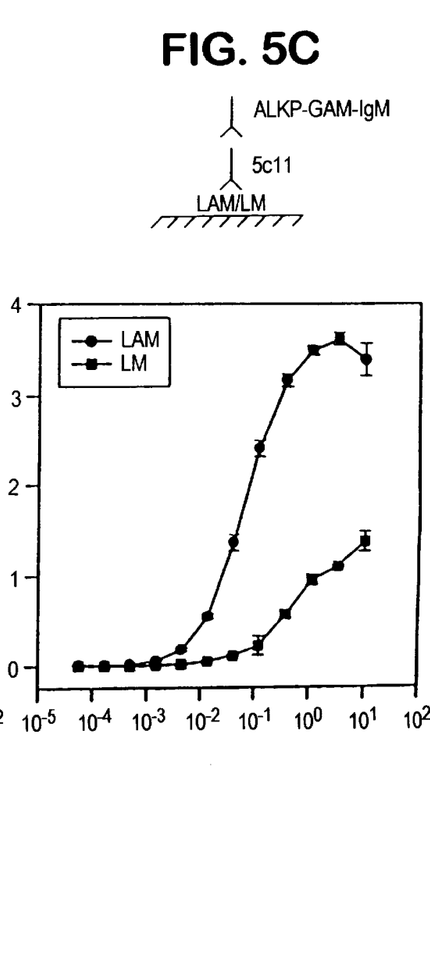
FIG. 5C: Comparative binding of 5c11 to LAM and LM at antigen concentration of 1 µg/ml. The diagram shows the ELISA configuration.
Figure 6A:
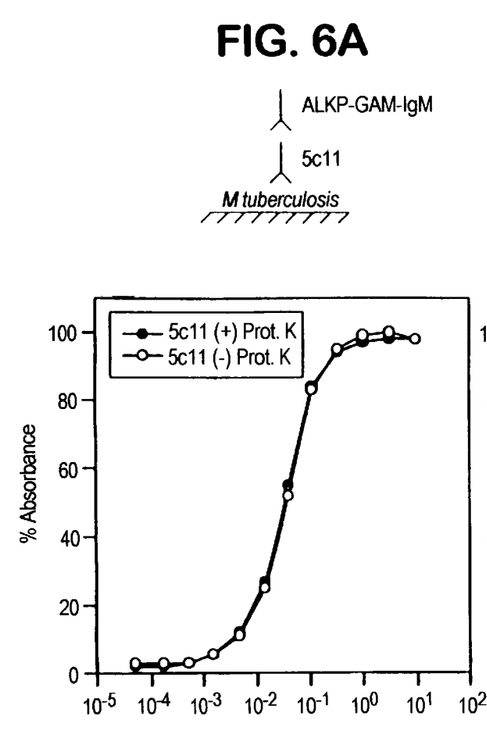
FIGS. 6A–6C set forth the binding of monoclonal antibodies to M. tuberculosis using whole cell ELISA with and without pre-treatment with Proteinase K. Filled symbols correspond to monoclonal antibody binding to proteinase K treated mycobacteria, whereas open symbols correspond to non-proteinase K treated mycobacteria.
Figure 6B:
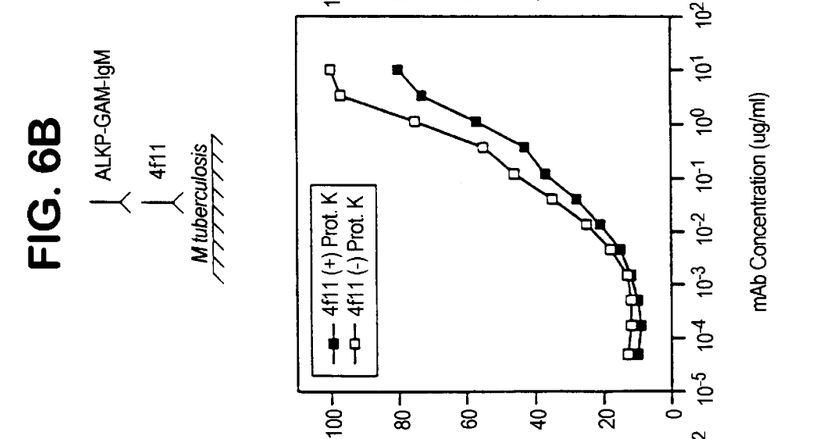
Figure 6C:
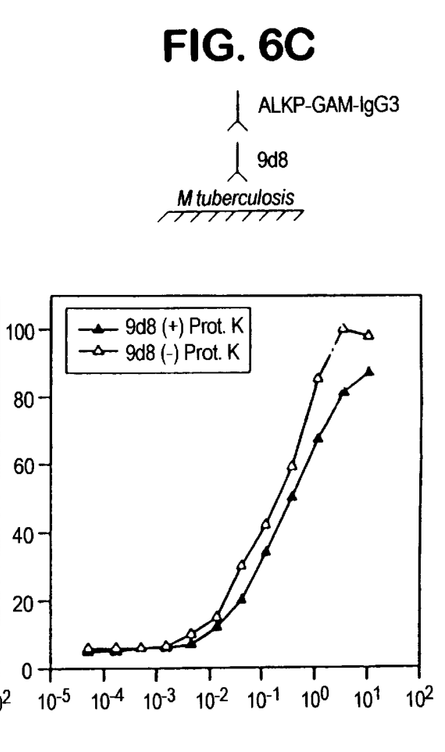

Epitope Chemical Analysis ELISAs. Sodium meta-periodate at acid pH causes mild oxidation of carbohydrate hydroxyl groups and opens sugar rings (Watt, et al., *J Infect Dis.* 158:681–686 (1988)). Treatment of whole cell *M. tuberculosis* with sodium meta-periodate resulted in reduced binding of monoclonal antibodies 5c11 and 4f11 to whole cell *M. tuberculosis* (FIG. 4) consistent with the presence of carbohydrates in the monoclonal antibodies epitopes. ELISAs performed with specific cell wall carbohydrates revealed that monoclonal antibodies 5c11 and 4f11 bound to mAGP (FIG. 5B) while only monoclonal antibody 5c11 bound LAM (FIG. 5A). Monoclonal antibody 5c11 bound significantly stronger to LAM than to LM at a monoclonal antibody concentration of 1 µg/ml (FIG. 5C). Proteinase K treatment of whole cell *M. tuberculosis* reduced the binding of monoclonal antibodies 9d8 and 4f11 but did not affect the binding of monoclonal antibody 5c11 (FIG. 6). None of the monoclonal antibodies bound PIM or TLF by ELISA.

Western blot analysis. None of the monoclonal antibodies reacted with mycobacterial antigens by Western Blot analysis, while the control monoclonal antibody to *M. tuberculosis* 70 kD heat shock protein showed a clear band.

Binding to other mycobacterial strains. Two methods were used for comparing monoclonal antibody binding to other mycobacterial strains: whole cell ELISA and indirect immunofluorescence. By whole cell ELISA both IgM monoclonal antibodies (5c11 and 4f11) bound to multiple mycobacterial strains. IgG3 monoclonal antibody 9d8 was more selective than the other monoclonal antibodies. In addition to binding the surface of *M. tuberculosis*, monoclonal antibody 9d8 also bound to *M. gordonae, M. gastri,* and *M. kansasii.* Indirect immunofluorescence demonstrated a similar trend. (Table 3).

TABLE 3

Binding of monoclonal antibodies to various mycobacterial and non-mycobacterial strains

| | 5c11 (IgM) | | 9d8 (IgG3) | | 4f11 (IgM) | |
|---|---|---|---|---|---|---|
| | ELISA* | IF | ELISA* | IF | ELISA* | IF |
| *M. tuberculosis* #1 | 1.000 | +++ | 1.000 | ++ | 1.000 | ND |
| *M. tuberculosis* #2 | 0.490 | ++ | 0.237 | ++ | 0.393 | ++ |
| *M. bovis*-BCG | 0.614 | +++ | 0.032 | − | 0.267 | +++ |
| *M. microti* | 0.493 | ++ | 0.160 | − | 0.166 | ++ |
| *M. avium* | 0.175 | ++ | 0.013 | − | 0.070 | ++ |
| *M. smegmatis* | 0.491 | +$_w$ | 0.036 | − | 0.414 | I |
| *M. xenopi* | 0.603 | ++ | 0.035 | − | 1.397 | ++ |
| *M. chitae* | 0.243 | ++ | 0.039 | − | 0.125 | + |
| *M. marinum* | 0.207 | + | 0.055 | − | 0.091 | − |
| *M. chelonae* | 0.377 | ++ | 0.050 | − | 0.199 | +++ |
| *M. gastri* | 0.720 | ++ | 0.710 | ++ | 0.975 | ++ |
| *M. kansasii* | 0.535 | ++ | 0.485 | + | 0.606 | + |
| *M. vaccae* | 0.368 | ++ | 0.017 | − | 0.044 | + |
| *M. phlei* | 0.592 | ++ | 0.027 | − | 0.096 | ++ |
| *M. fortuitum* | 1.054 | + | 0.096 | − | 1.237 | + |
| *M. terrae* | 0.092 | + | 0.105 | − | 0.318 | + |
| *M. szulgai* | 0.836 | ++ | 0.163 | − | 2.090 | ++ |
| *M. gordonae* | 0.879 | ++ | 0.955 | + | 1.871 | ++ |
| *Strep. pneumo.* | 0.000 | ND | 0.000 | ND | 0.002 | ND |
| *E. coli* | 0.000 | ND | 0.001 | ND | 0.017 | ND |
| *Coryneba. pseud.* | 0.002 | ND | 0.009 | ND | 0.009 | ND |
| *N. asteroides* | 0.049 | ND | 0.077 | ND | 0.109 | ND |
| *P. aeruginosa* | 0.000 | ND | 0.000 | ND | 0.000 | ND |
| *H. influenzae* | 0.001 | ND | 0.017 | ND | 0.031 | ND |

*ELISA comparison was done with optic density ratio using *M. tuberculosis* Erdman strain grown in PBT medium as reference.
IF-Indirect immunoforesence.
1-*M. tuberculosis* Erdman strain grown in PBT medium.
2-*M. tuberculosis* Erdman strain grown in LJ medium. IF using 3 clinical strains of *M. tuberculosis* grown in LJ medium gave similar results.
I-Indeterminate.
ND-Not done.
$_w$-Weak.

Figure 7A:
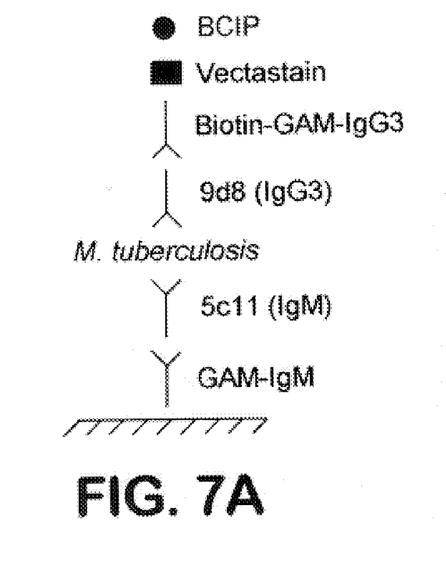
FIG. 7A shows a graphic representation of the ELISA assay configuration.
Figure 7B:
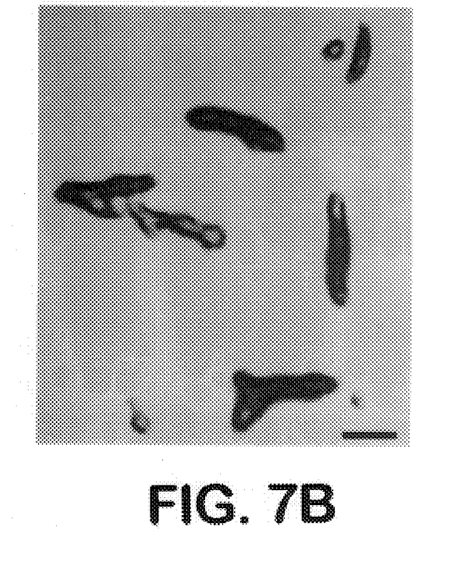
FIG. 7B sets forth a light microscopy image of M. tuberculosis captured and detected by the assay. Bar=5 µm. The picture was generated using Kodak RFS 2035 scanner and Adobe Photoshop version 3.0 for Macintosh.

Capture ELISA Spot Assay. A capture ELISA spot assay was developed by taking advantage of the fact that we had monoclonal antibodies of different specificity and isotype. The strong binding of monoclonal antibody 5c11 to *M. tuberculosis* suggested that it may be feasible to capture and immobilize mycobacteria. Mycobacteria captured by monoclonal antibody 5c11 were detected by monoclonal antibody 9d8 and visualized under light microscopy after staining. Monoclonal antibodies 5c11 and monoclonal antibody 9d8 recognize different epitopes, suggesting that the capture monoclonal antibody (5c11) would not interfere with the binding of the detecting monoclonal antibody (9d8). The use of the insoluble BCIP stained the immobilized mycobacteria blue and the use of slide chamber with removable cell walls allowed a 100×microscope lens to be used. This assay allowed the capture and visualization of single mycobacteria (FIG. 7).

Discussion

All 3 monoclonal antibodies generated in this study bound to the surface of *M. tuberculosis* as demonstrated by whole cell ELISA, indirect immunofluorescence and immunoelectronmicroscopy. The results of binding studies with defined mycobacterial fractions suggests that monoclonal antibodies 5c11 and 4f11 bind epitopes containing carbohydrates. Monoclonal antibody 5c11 binds both LAM and LM, but the stronger affinity for LAM relative to LM by ELISA suggests that the arabinose moiety is an important part of the epitope recognized. Both 5c11 and 4f 11 bind to mAGP—which is a fraction of the mycobacterial cell wall left after removing all soluble carbohydrates, proteins, and lipids (Wu, et al., *Chin. J. Microbiol. Immunol.* 22:173–180 (1989)). The strong binding of 5c11 to this complex is consistent with either the presence of LAM in the preparation or binding to arabinose which is found also in the mAGP complex. mAGP is known to be associated with protein in the mycobacterial cell wall skeleton in a complex called mycolyl-arabinogalactan-peptidoglycan-protein (mAGPP) (Wu, et al., *Chin. J. Microbiol. Immunol.* 22:173–180 (1989)). The reduction in binding of monoclonal antibody 4f11 to Proteinase K-treated *M. tuberculosis* suggests that Proteinase K digestion removed or destroyed part of the epitope recognized by this monoclonal antibody. For monoclonal antibody 9d8, no direct evidence was found for binding to protein, carbohydrate or lipid antigen. However, treatment of mycobacteria with proteinase K also reduced monoclonal antibody 9d8 binding, suggesting that the 9d8 epitope either contains or is attached to a protein moiety. No evidence for monoclonal antibody binding to protein was obtained by Western blot analysis for any of the 3 monoclonal antibodies. Hence, it may be concluded that monoclonal antibody 5c11 binds LAM, 4f11 binds a cell wall carbohydrate that belongs to the mAGP complex, and 9d8 binds a cell wall epitope of an uncertain composition which contains protein or is associated with protein. The results suggest however that protein is not a major component of the epitope recognized by monoclonla antibody 9d8.

The reactivity of the 3 monoclonal antibodies with 17 mycobacterial and 6 non-mycobacterial species was investigated. Monoclonal antibodies 9d8 and 5c11 were the most and least selective respectively, in their reactivity with different mycobacterial species. The low selectivity of monoclonal antibody 5c11 can be explained by the fact that most, if not all, mycobacterial strains contain LAM. None of the monoclonal antibodies bound to non-mycobacterial bacterial species. When interpreting the data in Table 3, it is important to consider that inter-species comparisons are difficult because there are differences in the adherence of mycobacterial species to polystyrene. This is not a problem for intra-species comparisons of 5c11, 9d8 and 4f11 binding. The ELISA and immunofluorescence binding results parallel each other for the majority of mycobacterial species. For some strains such as *M. avium* immunofluorescence and ELISA reactivity are significantly different. This problem is not understood but may reflect differences in epitope availability for mycobacteria attached to polystyrene or glass. The differences in monoclonal antibodies 5c11, 9d8 and 4f11 with individual strains are consistent with recognition of different epitopes by each monoclonal antibody.

Multiple protocols for direct ELISA (Mason, et al., *Tubercle Lung Dis.* 74:195–199 (1993); Schoningh, et al., *J. Clin. Microbiol.* 28: 708–713 (1990); Verstijnen, et al., *J. Clin. Microbiol.* 29:1372–1375 (1991)), capture ELISA (Cho, et al., *Yonsei Med. J.* 31:333–338 (1990); Cho, et al., *J. Clin. Microbiol.* 30: 3065–3069 (1992); Friedman, et al., *Am. Rev. Respir. Dis.* 140: 668–671 (1989); Kadival, et al., *J. Clin. Microbiol.* 23: 901–904 (1986); Rattan, et al., *Tubercle Lung Dis.* 74: 200–203 (1993); Sada, et al., *Lancet* 2 651–652 (1983); Watt, et al., *J Infect Dis.* 158:681–686 (1988); Wu, et al., *Chin. J. Microbiol. Immunol.* 22:173–180 (1989); Yanez, et al., *J. Clin. Microbiol.* 23: 822–825 (1986)) and DOT ELISA (Cho, et al., *J. Clin. Microbiol.* 30: 3065–3069 (1992); Papa, et al., *Res. Microbiol.* 143: 327–331 (1992)) have been described for the detection of mycobacteria and their antigens. The assay described herein differs from those assays in several aspects. First, the modified ELISA spot assay of the present invention combines ELISA technology with light microscopy. Second, this is the first assay that applies the ELISA spot technique to the detection of microorganisms and allows visualization of single captured organisms. The use of two monoclonal antibodies avoids the need to use polyclonal immunoglobulins which have the potential disadvantage of lot to lot variation, reliance on animal sources and unwanted cross-reactivities. The use of monoclonal antibodies to different mycobacterial epitopes prevents competition by the detecting monoclonal antibody (9d8) and the capture monoclonal antibody (5c11), and should, in theory, increase sensitivity. Furthermore, the combination of a broadly cross reactive, high affinity monoclonal antibody (5c11) with a more selective monoclonal antibody (9d8) has the potential for offering sensitivity and specificity when analyzing clinical specimens. An additional advantage is the simplicity of the assay in terms of equipment and personnel required for its use. In addition to the adapted slide chamber, this assay requires only ELISA reagents and a light microscope. Completion of the assay required 1.5 days in the laboratory. This assay offers a very useful tool for the detection of *M. tuberculosis*. The simplicity of the assay could be an advantage in laboratories where access to complex and expensive technology or instrumentation is not possible due to cost, such as may be the case in many developing countries.

All publications mentioned hereinabove are hereby incorporated by reference in their entirety.

While the foregoing invention has been described in detail for purpose of clarity and understanding, it will be appreciated by one skilled in the art from a reading of the disclosure that various changes in form and detail can be made without departing from the true scope of the invention in the appended claims.

What is claimed is:

1. A monoclonal antibody which does not bind to *Mycobacterium avium* and which binds to the same *Mycobacterium tuberculosis* surface epitope as the monoclonal antibody produced by hybridoma cell line H-9d8 having ATCC Accession No. HB-12364.

2. The monoclonal antibody of claim 1 which is conjugated to a label.

3. The monoclonal antibody of claim 2 wherein the label is a cytotoxic agent, an antibiotic, or a detectable marker.

4. The monoclonal antibody of claim 3 wherein the detectable marker is a radioisotope or an enzyme.

5. A monoclonal antibody produced by hybridoma cell line H-9d8 having ATCC Accession No. HB-12364.

6. The monoclonal antibody of claim 5, which is conjugated to a label.

7. The monoclonal antibody of claim 6, wherein the label is a cytotoxic agent, an antibiotic, or a detectable marker.

8. The monoclonal antibody of claim 7, wherein the detectable marker is a radioisotope or an enzyme.

9. The monoclonal antibody of claim 1, wherein the monoclonal antibody is made by a process comprising at least one whole cell immunization and wherein the whole cells are heat-inactivated before immunization.

10. The monoclonal antibody of claim 1, wherein the monoclonal antibody is made by a process comprising at least one whole cell immunization and wherein the whole cells are sonicated before immunization.

11. The monoclonal antibody of claim 1, wherein the monoclonal antibody is made by a process comprising at least one whole cell immunization and wherein the whole cells are heat-inactivated and sonicated before immunization.

12. A fragment of the monoclonal antibody of claim 1, wherein the fragment binds to the same *Mycobacterium tuberculosis* surface epitope as the monoclonal antibody.

* * * * *